US012569534B2

(12) United States Patent
Hu et al.

(10) Patent No.: US 12,569,534 B2
(45) Date of Patent: Mar. 10, 2026

(54) THERAPEUTIC NANOPARTICLES BY COACERVATE COMPLEXATION AND THEIR USE FOR TREATING BACTERIA

(71) Applicant: Academia Sinica, Taipei (TW)

(72) Inventors: Che-Ming Jack Hu, Taipei (TW); Yu-Han Liu, Taipei (TW); Te-Li Chen, Taipei (TW)

(73) Assignee: ACADEMIA SINICA, Taipei (TW)

( * ) Notice: Subject to any disclaimer, the term of this patent is extended or adjusted under 35 U.S.C. 154(b) by 1275 days.

(21) Appl. No.: 17/265,090

(22) PCT Filed: Jul. 30, 2019

(86) PCT No.: PCT/US2019/044067
§ 371 (c)(1),
(2) Date: Feb. 1, 2021

(87) PCT Pub. No.: WO2020/028319
PCT Pub. Date: Feb. 6, 2020

(65) Prior Publication Data

US 2021/0315966 A1 Oct. 14, 2021

Related U.S. Application Data

(60) Provisional application No. 62/712,068, filed on Jul. 30, 2018.

(51) Int. Cl.

*A61K 38/12* (2006.01)
*A61K 9/16* (2006.01)
*A61P 31/04* (2006.01)

(52) U.S. Cl.
CPC ............ *A61K 38/12* (2013.01); *A61K 9/1617* (2013.01); *A61K 9/1641* (2013.01);
(Continued)

(58) Field of Classification Search
CPC .... A61K 38/12; A61K 9/1617; A61K 9/1641; A61K 9/1647; A61K 9/1652;
(Continued)

(56) References Cited

U.S. PATENT DOCUMENTS 9,642,803 B2 5/2017 Linder et al.
9,789,194 B2 10/2017 Devore et al.
(Continued)

FOREIGN PATENT DOCUMENTS

WO WO-2017/089942 A1 6/2017

OTHER PUBLICATIONS

Wang et al., Electrostatic interactions between polyglutamic acid and polylysine yields stable polyion complex micelles for deoxypodophyllotoxin delivery. Int J Nanomedicine. Oct. 30, 2017; 12:7963-7977. doi: 10.2147/IJN.S140573. PMID: 29133981; PMCID: PMC5669785 (Year: 2017).*
(Continued)

*Primary Examiner* — Randall L Beane
(74) *Attorney, Agent, or Firm* — Birch, Stewart, Kolasch & Birch, LLP

(57) ABSTRACT

A therapeutic nanoparticle containing a cationic polypeptide and a polyanionic molecule, in which the cationic polypeptide, exerting antibacterial activity, forms electrostatic interaction with the polyanionic molecule, and the therapeutic nanoparticle has diameter of less than 50 mun. Also disclosed are a pharmaceutical composition, a treatment method, and a preparation method, all related to the therapeutic nanoparticle.

8 Claims, 7 Drawing Sheets

(52) U.S. Cl.
CPC .......... *A61K 9/1647* (2013.01); *A61K 9/1652* (2013.01); *A61K 9/1658* (2013.01); *A61K 9/1694* (2013.01); *A61P 31/04* (2018.01)

(58) Field of Classification Search
CPC ................ A61K 9/1658; A61K 9/1694; A61K 38/1729; A61K 47/645; A61K 47/6935; A61P 31/04; Y02A 50/30
See application file for complete search history.

(56) References Cited

U.S. PATENT DOCUMENTS

| | | | | |
|---|---|---|---|---|
| 2005/0252773 | A1* | 11/2005 | McBride | C12Q 1/68 204/450 |
| 2007/0224280 | A1* | 9/2007 | Lillard | A61K 33/244 424/490 |
| 2009/0169635 | A1 | 7/2009 | Schwarz et al. | |
| 2011/0250237 | A1* | 10/2011 | O'Hagan | C07K 14/005 424/282.1 |
| 2013/0045162 | A1* | 2/2013 | Lillard, Jr. | A61P 35/00 977/773 |
| 2013/0122103 | A1* | 5/2013 | Kishimura | C08G 81/00 424/497 |
| 2013/0183379 | A1 | 7/2013 | Devore et al. | |
| 2013/0259924 | A1* | 10/2013 | Bancel | C07K 14/705 530/358 |
| 2016/0058775 | A1 | 3/2016 | Prasad et al. | |
| 2016/0230189 | A1 | 8/2016 | Kotha et al. | |
| 2017/0042823 | A1 | 2/2017 | Prud'homme et al. | |
| 2017/0280712 | A1* | 10/2017 | Lillard, Jr. | A01N 43/54 |

OTHER PUBLICATIONS

Insua et al., Preparation and antimicrobial evaluation of polyion complex (PIC) nanoparticles loaded with polymyxin B. Eur Polym J. Feb. 2017;87:478-486 and 4 pages of Supplemental Data. doi: 10.1016/j.eurpolymj.2016.08.023. PMID: 28280277; PMCID: PMC5327956 (Year: 2017).*

O'Connell et al., Association behavior of β-casein. Journal of Colloid and Interface Science. vol. 258:33-39 (2003) . 10.1016/S0021-9797(02)00066-8 (Year: 2003).*

Maguire et al., Characterisation of particles in solution—a perspective on light scattering and comparative technologies. Sci Technol Adv Mater. Oct. 18, 2018;19(1):732-745. doi: 10.1080/14686996.2018.1517587. PMID: 30369998; PMCID: PMC6201793 (Year: 2018).*

Primavera et al., Laser diffraction and light scattering techniques for the analysis of food matrices. Biomed International—Advances In Food Safety And Health. vol. 6:40-60 (2014) (Year: 2014).*

Wu et al., Stabilization of naked and condensed plasmid DNA against degradation induced by ultrasounds and high-shear vortices. Biotechnol Appl Biochem. Jun. 22, 2009;53(Pt 4):237-46. doi: 10.1042/BA20080215. PMID: 19228116 (Year: 2009).*

Kakizawa et al., Environment-Sensitive Stabilization of Core-Shell Structured Polyion Complex Micelle by Reversible Cross-Linking of the Core through Disulfide Bond, J. Am. Chem. Soc. 1999, 121, 48, 11247-11248 (Year: 1999).*

Colville et al., Effects of poly(L-lysine) substrates on attached *Escherichia coli* bacteria. Langmuir. Feb. 16, 2010;26(4):2639-44. doi: 10.1021/la902826n. PMID: 19761262 (Year: 2010).*

Luger et al., Crystal structure of the nucleosome core particle at 2.8 A resolution. Nature. Sep. 18, 1997;389(6648):251-60. doi: 10.1038/38444. PMID: 9305837 (Year: 1997).*

Hoeksema et al, Histones as mediators of host defense, inflammation and thrombosis. Future Microbiol. 2016;11(3):441-53. doi: 10.2217/fmb.15.151. Epub Mar. 4, 2016. PMID: 26939619; PMCID: PMC5549641 (Year: 2016).*

Pertinhez et al., The micelle-bound structure of an antimicrobial peptide derived from the alpha-chain of bovine hemoglobin isolated from the tick Boophilus microplus. Biochemistry. May 3, 2005;44(17):6440-51. doi: 10.1021/bi0475323. PMID: 15850378 (Year: 2005).*

Pergushov et al., Micellar interpolyelectrolyte complexes. Chem Soc Rev. Nov. 7, 2012;41(21):6888-901. doi: 10.1039/c2cs35135h. PMID: 22814675 (Year: 2012).*

Che et al., DSPE-PEG: a distinctive component in drug delivery system. Curr Pharm Des. 2015;21(12):1598-605. doi: 10.2174/1381612821666150115144003. PMID: 25594410 (Year: 2015).*

Insua et al., Polyion complex (PIC) particles: Preparation and biomedical applications. Eur Polym J. Aug. 2016;81:198-215. doi: 10.1016/j.eurpolymj.2016.06.003. PMID: 27524831; PMCID: PMC4973809 (Year: 2016).*

Moss et al., "Glossary of class names of organic compounds and reactivity intermediates based on structure (IUPAC Recommendations 1995)" Pure and Applied Chemistry, vol. 67, No. 8-9, 1995, pp. 1307-1375 (Year: 1995).*

He et al., Magnetic separation techniques in sample preparation for biological analysis: A review, Journal of Pharmaceutical and Biomedical Analysis, vol. 101, 2014, pp. 84-101, ISSN 0731-7085, https://doi.org/10.1016/j.jpba.2014.04.017 (Year: 2014).*

Jolly et al., Oligonucleotide-based systems: DNA, microRNAs, DNA/RNA aptamers. Essays Biochem. Jun. 30, 2016;60(1):27-35. doi: 10.1042/EBC20150004. PMID: 27365033; PMCID: PMC4986462 (Year: 2016).*

Ignacio Insua Lopez, Polyion complex (PIC) nanoparticles for the targeted and passive delivery of antimicrobial polymers and peptides, University of Birmingham, Doctoral Dissertation, 149 pages, (Feb. 2017) (Year: 2017).*

Wallace et al., Drug release from nanomedicines: Selection of appropriate encapsulation and release methodology. Drug Deliv Transl Res. Aug. 2012;2(4):284-92. doi: 10.1007/s13346-012-0064-4. Epub Mar. 3, 2012. PMID: 23110256; PMCID: PMC3482165 (Year: 2012).*

Din et al., Effective use of nanocarriers as drug delivery systems for the treatment of selected tumors. Int J Nanomedicine. Oct. 5, 2017;12:7291-7309. doi: 10.2147/IJN.S146315. PMID: 29042776; PMCID: PMC5634382 (Year: 2017).*

Tong et al., Self-assembly of phospholipid-PEG coating on nanoparticles through dual solvent exchange. Nano Lett. Sep. 14, 2011; 11(9):3720-6. doi: 10.1021/nl201978c. Epub Aug. 1, 2011. PMID: 21793503; PMCID: PMC3173588 (Year: 2011).*

Insua et al "Preparation and Antimicrobial Evaluation of Polyion Complex (PIC) Nanoparticles Loaded with Polymyxin B" European Polymer Journal vol. 87, pp. 478-286, 2017.

Liu et al "Colistin Nanoparticle Assembly by Coacervate Complexation with Polyanionic Peptides for Treating Drug-Resistant Gram-Negative Bacteria" Acta Biomaterialia vol. 82, pp. 133-142, 2018.

* cited by examiner

A.

THERAPEUTIC NANOPARTICLES BY COACERVATE COMPLEXATION AND THEIR USE FOR TREATING BACTERIA

CROSS REFERENCE TO RELATED APPLICATIONS

This application is the National Stage of International Application No. PCT/US2019/044067, filed on Jul. 30, 2019, which claims priority to U.S. Provisional Application No. 62/712,068, filed on Jul. 30, 2018, the contents of both prior applications being hereby incorporated by reference in their entirety.

BACKGROUND

Treatment of bacterial infections faces significant challenges due to emergence of antibiotic resistance. For example, carbapenem-resistant *Acinetobacter baumannii, Pseudomonas aeruginosa*, and Enterobacteriaceae are three gram-negative bacteria that pose serious threats to human health. See Willyard, *Nature*, 2017, 543, 15. These bacteria cause various diseases, including pneumonia, bacteremia, meningitis, urinary tract, and skin and wound infection. See Bergogne-Berezin et al., *Clin. Microbiol. Rev.*, 1996, 9, 148-165 and Guzek et al., *Adv. Exp. Med. Biol.*, 2017, 955, 39-46.

As carbapenem is often used as the last line of therapy against lethal bacterial infections, its waning efficacy has prompted major research efforts for alternative antimicrobials in treating certain bacteria. See Antachopoulos et al., *Pediatr. Infect. Dis. J.*, 2017, 36, 905-907. Among the alternatives, colistin, a decade-old antimicrobial, is gaining increasing interest as few other options show comparable efficacy against gram-negative bacteria. See Montero et al., *The J. Antimicrob. Chemother.*, 2004, 54, 1085-1091. As a member of polymyxins, colistin is a mixture of polycationic cyclic peptides with potent antibacterial activities attributable to the strong electrostatic interaction with bacterial membranes. See Colomb et al., *Int. J. Pharm.*, 1993, 90, 59-71. Colistin has been increasingly used as an antimicrobial for treating multidrug-resistant gram-negative bacteria, yet its side effects of nephrotoxicity and neurotoxicity pose significant safety concerns. See Falagas et al., *Expert Rev. Anti-Infect. Ther.*, 2018, 6, 593-600.

Colistin has been chemically modified and formulated for improving its safety profile. For instance, colistin prodrug and derivative have been synthesized through methanesulfonate modification and replacement of amines with non-cationic residues. See Li et al., *Journal of Antimicrobial Chemotherapy*, 2003, 52, 987-992; Li et al., *J. Antimicrob. Chemother.*, 2004, 53, 837-840; Vaara et al., *Antimicrob. Agents Chemother.*, 2008, 52, 3229-3236; Vaara et al., *J.* Antimicrob. Chemother., 2013, 68, 636-639; and Vaara et al., *Peptides*, 2010, 31, 2318-2321.

Charge reduction in these derivatives results in improved drug safety but also causes loss in antimicrobial efficacy.

Nanoparticle drug delivery platforms, e.g., liposomes and polymeric nanoparticles, have been extensively exploited to enhance therapeutic effectiveness and lower side effects of existing antibiotics. Indeed, colistin has been formulated with a number of nanoparticle platforms, including quantum dots, liposomes, poly(lactic-co-glycolic acid)-particles, silica nanoparticles, and poly(styrene sulphonate) particles. See Carrillo-Carrion et al., *Biosens. Bioelectron.*, 2011, 26, 4368-4374; Wallace et al., *Drug Delivery and Translational Research*, 2012, 2, 284-292; Wallace et al., *J. Pharm. Sci.*, 2012, 101, 3347-3359; Shah et al., *Pharm. Res.*, 2014, 31, 3379-3389; Gounani et al., *Int. J. Pharm.*, 2018, 537, 148-161; Insua et al., *Eur. Polym. J.*, 2017, 87, 478-486; and Insua et al., *Sci. Rep.*, 2017, 7, 9396. However, in many instances, nanocarrier-associated colistin exhibits lowered antimicrobial activity.

There is a need to develop a new nanocarrier system for delivering an antibiotic that improves its therapeutic efficacy while exerting a desirable safety profile.

SUMMARY

An aspect of the present invention is a therapeutic nanoparticle containing a cationic polypeptide and a polyanionic molecule. The cationic polypeptide, exerting antibacterial activity, forms electrostatic interaction with the polyanionic molecule, and the therapeutic nanoparticle has a diameter of less than 50 nm. Unexpectedly, the therapeutic nanoparticle enhances the therapeutic effectiveness of the cationic polypeptide, i.e., colistin, with an improved safety profile.

Typically, the cationic polypeptide is an antibiotic selected from the group consisting of colistin, polymyxin B, and polymyxin M. An exemplary therapeutic nanoparticle contains colistin as the cationic polypeptide.

On the other hand, the polyanionic molecule can be an anionic polypeptide, an anionic oligonucleotide, an anionic polynucleotide, or an anionic polyorganic acid. For example, the polyanionic molecule is a plasmid having a size of less than 10,000 base pairs or bp (e.g., less than 6,000 bp, less than 500 bp, and less than 20 bp). As another example, the polyanionic molecule is an antisense oligonucleotide. In addition, the polyanionic molecule also can be a diblock copolymer containing a polyethyleneglycol (PEG) and an anionic polypeptide.

Notably, the therapeutic nanoparticle can further contain an amphiphilic stabilizer. In general, the amphiphilic stabilizer is a PEG lipid. Examples of a PEG lipid include, but are not limited to, distearoyl-sn-glycero-3-phosphoethanolamine-polyethyleneglycol (DSPE-PEG), DSPE-PEG-Maleimide, DSPE-PEG-Biotin, methoxyPEG-Cholesterol (mPEG-Cholesterol), and Cholesterol-PEG-Amine.

The therapeutic nanoparticle described above typically includes the cationic polypeptide and the polyanionic molecule having a cation:anion charge ratio of 1:4 to 7:1 (e.g., 1:2, 1:1, 2:1, and 4:1).

Another aspect of this invention is a pharmaceutical composition containing a therapeutic nanoparticle set forth above and a pharmaceutically acceptable carrier.

Further covered by this invention is a method of preparing the therapeutic nanoparticle. The method includes: providing an aqueous solution that contains an amphiphilic stabilizer, mixing into the aqueous solution a cationic polypeptide and a polyanionic molecule in a pre-determined molar ratio, and obtaining a therapeutic nanoparticle from the resultant mixture.

Still within the scope of this invention is a method of treating gram-negative bacteria, the method including administering to a subject in need thereof an effective amount of the above-described therapeutic nanoparticle.

The details of the invention are set forth in the description below. Other features, objects, and advantages of the invention will be apparent from the following drawings and detailed description of several embodiments, and also from the appending claims.

DESCRIPTION OF THE DRAWINGS

FIG. 1D is a graph showing the numbers of CFUs in blood, heart, liver, spleen, lung, and kidney in two different treatment groups, i.e., mice treated with 5 mg/kg of CS or 20 mg/kg CS NPs, which were monitored and analyzed by one-way analysis of variance (error bars represent means±s.e.m; n=3).

DETAILED DESCRIPTION

Figure 1:
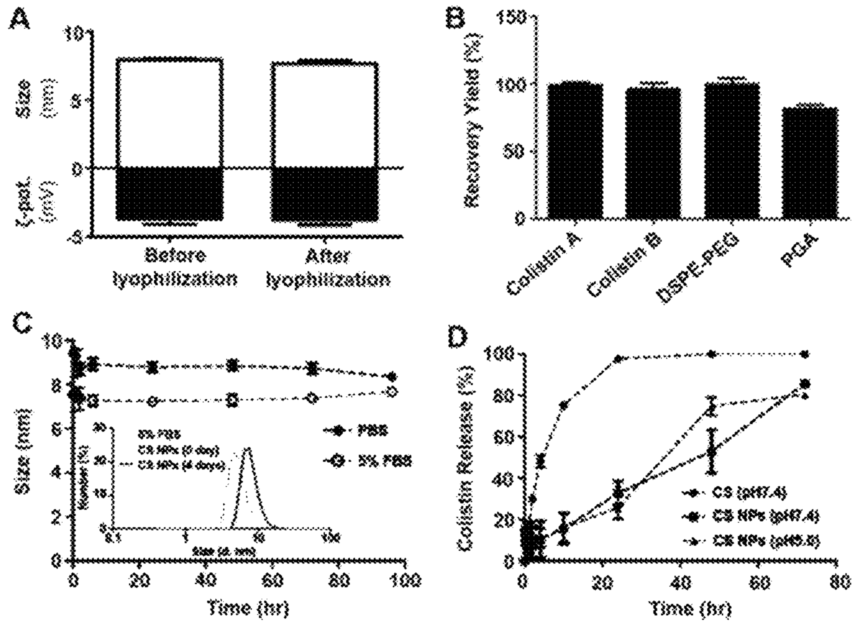
FIG. 1A is a graph showing the size and zeta potential of colistin nanoparticles (CS NPs) before and after lyophilization (n=3)
FIG. 1B is a graph showing the recovery yield of colistin A, colistin B, DSPE-PEG, and polyglutamic acids in CS NPs (n=3)
FIG. 1C is a graph showing size measurements of CS NPs in phosphate-buffered saline (PBS) and in 5% fetal bovine serum (FBS) solutions at 25° C. for 4 days, inset highlighting distinctive size distributions between FBS proteins and colistin nanoparticles in FBS (n=3)
FIG. 1D is a graph showing colistin (CS) release from CS NPs at pH 7.4 and pH 5 (n=3), error bars representing means±standard deviation.

Disclosed first in detail herein is a therapeutic nanoparticle that unexpectedly enhances the therapeutic effectiveness of an antibiotic (i.e., colistin) with an improved safety profile.

As set forth above, the therapeutic nanoparticle of this invention contains a cationic polypeptide and a polyanionic molecule, in which cationic polypeptide, exerting antibacterial activity, forms electrostatic interaction with the polyanionic molecule.

The therapeutic nanoparticle has a diameter of less than 50 nm, preferably, less than 25 nm, and more preferably, less than 15 nm.

Examples of the cationic polypeptide include, but are not limited to, colistin (i.e., polymyxin E), polymyxin B, and polymyxin M.

Again, the polyanionic molecule typically is an anionic polypeptide, an anionic oligonucleotide, an anionic polynucleotide, or an anionic polyorganic acid.

In one embodiment, the polyanionic molecule is a polyamino acid formed from glutamic acid, i.e., polyglutamic acid (PGA), or aspartic acid, i.e., polyaspartic acid (PLD). It can also be a polymer formed from one or more glutamic acids or aspartic acids with one or more other amino acids (e.g., alanine, cysteine, and tyrosine).

In another embodiment, the polyanionic molecule is a single- or double-stranded deoxyribonucleic acid (DNA), a ribonucleic acid, or a locked nucleic acid. For example, the polyanionic molecule is a 20-mer double-stranded DNA. As another example, the polyanionic molecule is a plasmid having a size of less than 10,000 bp (e.g., less than 6,000 bp, less than 500 bp, and less than 20 bp). As yet another example, the polyanionic molecule is an antisense oligonucleotide.

In a further embodiment, the polyanionic molecule is a diblock copolymer containing a PEG and an anionic polypeptide, in which the anionic polypeptide can be a polyamino acid formed from glutamic acid or aspartic acid. An exemplary therapeutic nanoparticle containing a diblock copolymer is formed from colistin and PEG-polyaspartic acid (PEG-PLD).

As pointed out above, the therapeutic nanoparticle of this invention can further contain an amphiphilic stabilizer, which typically is a PEG lipid. Examples of a PEG lipid include, but are not limited to, DSPE-mPEG, DSPE-PEG- Maleimide, DSPE-PEG-Biotin, mPEG-Cholesterol, and Cholesterol-PEG-Amine. Their structures are shown below.
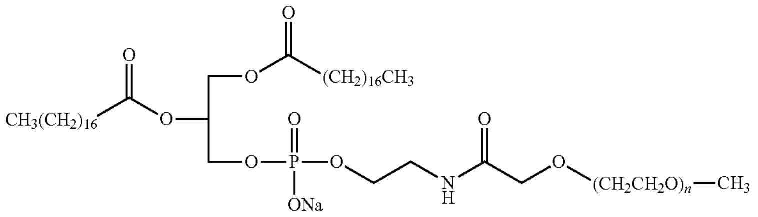
DSPE-mPEG (molecular weight: 1k-40k)
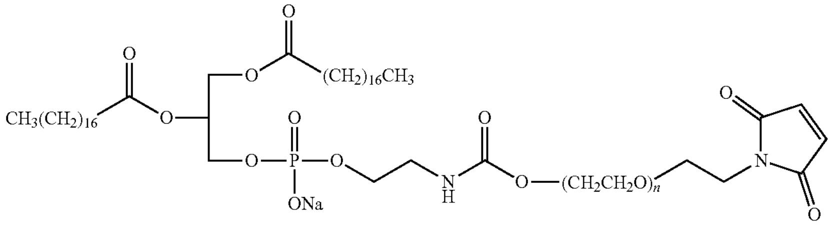
DSPE-PEG-Maleimide (molecular weight: 1k-5k)
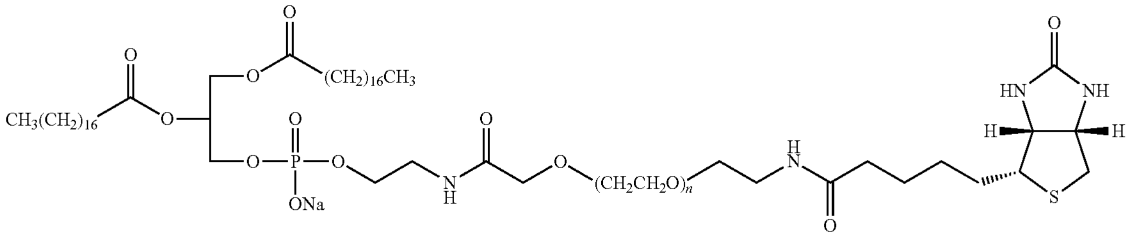
DSPE-PEG-Biotin (molecular weight: 1k-5k)
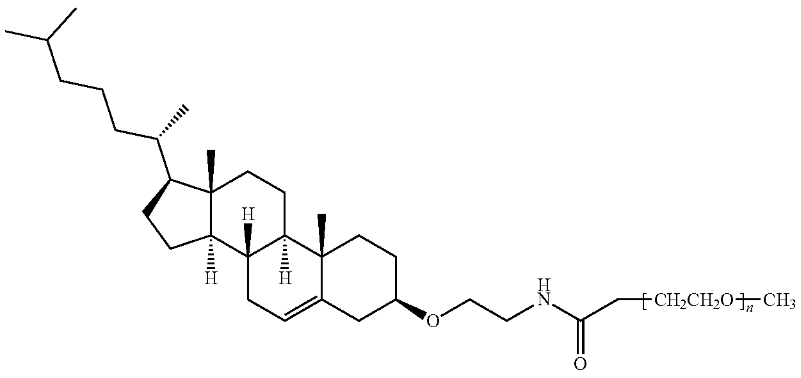
mPEG-Cholesterol (molecular weight: 1k-40k)
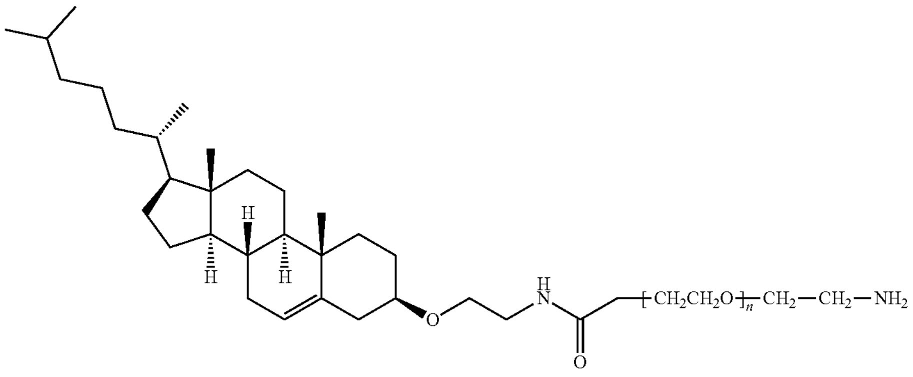
Cholesterol-PEG-Amine (molecular weight: 1k-10k)

Of note, the therapeutic nanoparticle described above typically includes a cationic polypeptide and a polyanionic molecule having a cation:anion charge ratio of 1:4 to 7:1, preferably, 1:1 to 7:1.

In a preferred embodiment, the therapeutic nanoparticle further contains an amphiphilic stabilizer and has a diameter of less than 15 nm, the cationic polypeptide and the polyanionic molecule have a cation:anion charge ratio of 1:4 to 7:1, and the polyanionic molecule is an anionic polypeptide, an anionic oligonucleotide, an anionic polynucleotide, or an anionic polyorganic acid.

Also disclosed is a pharmaceutical composition containing the above therapeutic nanoparticle and a pharmaceutically acceptable carrier.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active glycoside compound. Examples of other carriers include colloidal silicon oxide, magnesium stearate, cellulose, sodium lauryl sulfate, and D&C Yellow #10.

Still covered by this invention is a method of preparing the therapeutic nanoparticle. The method includes the following steps: (i) providing an aqueous solution that contains an amphiphilic stabilizer, (ii) mixing into the aqueous solution a cationic polypeptide and a polyanionic molecule in a pre-determined molar ratio, and (iii) obtaining a therapeutic nanoparticle from the resulted mixture.

To prepare the therapeutic nanoparticle, the cationic polypeptide and polyanionic molecule are typically mixed in a molar ratio of 1.6:1 to 518:1.

Finally, this invention also covers a method for treating gram-negative bacteria, the method including administering to a subject (e.g., a patient) in need thereof an effective amount of the above-described therapeutic nanoparticle.

The term "an effective amount" refers to the amount of complexes that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of the present invention, a composition having the above-described nanoparticles can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition containing the nanoparticles can also be administered in the form of suppositories for rectal administration.

Without further elaboration, it is believed that one skilled in the art can, based on the above description, utilize the present invention to its fullest extent. The following specific examples, i.e., EXAMPLES 1-4, are therefore to be construed as merely illustrative, and not limitative of the remainder of the disclosure in any way whatsoever. All publications cited herein are incorporated by reference in their entirety.

All reagents and chemicals were analytical grade. Colistin sulfate salt, poly-L-glutamic acid sodium salt (MW 3000-15000), acetonitrile, trifluoroacetic acid (TFA), bovine serum albumins, sodium phosphate monobasic monohydrate, sodium phosphate dibasic anhydrous were purchased from Sigma-Aldrich (St. Louis, MO). Sodium acetate anhydrous was purchased from Merck (Darmstadt, Germany). 1,2-Dimyristoyl-sn-glycero-3-phosphoethanol amine-N-[methoxy (polyethylene glycol)-2000](ammonium salt) (DSPE-PEG2000; molecular weight: 2693.285 Da) and 1,2-Dimyristoyl-sn-glycero-3-phosphoethanol amine-N-[methoxy (polyethylene glycol)-5000](ammonium salt) (DSPE-PEG5000; molecular weight: 5797.04 Da) were purchased from Avanti Polar Lipids (Alabaster, AL). Alexa Fluor 647 and Alexa Fluor 488 were purchased from Thermo Fisher Scientific (Invitrogen, Carlsbad, CA). Methoxy-poly (ethylene glycol)-block-poly(L-aspartic acid sodium salt) [number of ethylene glycol Repeating Units: n=454 (MW=20,000 Da); number of aspartic acid repeating units: x=75 (MW=10,500 Da)] was purchased from Alamanda Polymers (Huntsville, AL). Antisense oligonucleotides were synthesized from Eurogentec (5'→3') (Cy5-mCmCmAmU-TG-GTT-CAA-A-mCmAmUmA, m_: 2' O-methyl bases).

Example 1: Nanoparticles Formed from Colistin, PGA, and DSPE-PEG2000

A study was performed as follows for preparing, characterizing, and testing therapeutic nanoparticles formed from colistin (CS), PGA, and DSPE-PEG2000.

To induce coacervation between the cationic CS and the anionic PGA, a screening assay was carried out by mixing the two components at different weight ratios. At CS:PGA ratios below 5:5, no phase separation was observed. Upon increasing CS:PGA ratios to above 6:4, the resultant solution became cloudy and exhibited formation of liquid droplets. As the CS:PGA ratio increased between 6:4 to 9:1, the average size of the droplets increased from ~300 nm to ~20,000 nm with a corresponding increase in zeta potential from −20 mV to 2 mV. Coacervate formation was not observed when the CS:PGA ratio was between 0:10 to 6:4 or between 9:1 to 10:0. Upon validating coacervate complexation between CS and PGA, CS nanoparticles (CS NPs) were prepared with the CS:PGA weight ratio being 6:4 as the mixture yielded the smallest coacervate droplets with a negative zeta potential.

In a typical preparation, 3.6 mg of CS and 2.4 mg of PGA were mixed in 7.2 mL of water containing 36 mg of DSPE-PEG2000. The mixture was then dispersed using a high-pressure homogenizer Nanolyzer-N2 (Gogene Corporation; Hsinchu County, Taiwan) operating at 5,000 psi. The resulting nanoparticles were filtered to remove free CS, PGA, or DSPE-PEG using a 30 kDa MWCO Amicon® Ultra Centrifugal Filter (Merck Millipore; County Cork, Ireland).

The nanoparticles were subsequently analyzed for their physicochemical properties. Dynamic light scattering (DLS) measurements showed that the CS NPs had a diameter of 8 nm and a zeta potential of −3 mV, and there was no change in size or zeta potential following lyophilization and reconstitution in water (FIG. 1A). High performance liquid chromatography (HPLC) analysis of the content of the CS NPs showed that the recovery yield for colistin A, colistin B, DSPE-PEG, and PGA were 99.07, 95.74, 99.60 and 81.45, respectively (FIG. 1B), indicating highly efficient CS incorporation into the nanoparticles.

The nanoparticles were also assessed for stability. It was found that they remained stable in PBS and 10% FBS solutions at room temperature for at least 4 days without exhibiting size alteration (FIG. 1C).

CS release from the CS NPs was studied using a dialysis tube with 50 k MWCO membrane (Pur-A-Lyzer™ Maxi Dialysis Kit, Sigma-Aldrich) in 0.15 M phosphate buffer (pH 7.4) and in 0.15 M acetate buffer solution (pH 5.0). The phosphate buffer contained 16.48 g/L $Na_2HPO_4$ and 4.67 g/L $NaH_2PO_4$ and the acetate buffer solution contained 0.3% (v/v) acetic acid and 1.3% (w/v) sodium acetate. Samples were each placed into a dialysis tube at 37° C. under gentle stirring. At predetermined time points, the samples were collected and analyzed for CS content using HPLC.

It was found that while free CS was rapidly dialyzed from the setup, the CS NPs showed a sustained release profile and retained 70% of the CS content after 24 hours (FIG. 1D). Between pH 7.4 and pH 5.0, no significant difference in release kinetics was observed. As the pKa of the amine groups on CS is about 10 and that of the carboxylic groups on PGA is about 4.3, the two molecules are expected to retain their opposing charges at pH 7.4 and pH 5.0. Variation in acidity at the physiological level is therefore not expected to significantly influence the complexation dynamics.

Antibacterial Efficacy of CS NPs

To evaluate antibacterial efficacy of the CS NPs, their minimum inhibitory concentration (MIC) and minimum bactericidal concentration (MBC) were assessed against 5 reference bacterial strains and 39 clinical isolates of carbapenem-resistant *A. baumannii, P. aeruginosa, E. coli*, and *K. pneumoniae.*

Reference bacterial stains were purchased from ATCC. Clinical isolates of carbapenem-resistant bacteria were obtained from National Health Research Institutes (NHRI) and Tri-Service General Hospital (TSGH). MIC is defined as the lowest concentration of antibiotics required to inhibit the growth of bacteria. MBC is defined as the lowest concentration of antibiotics required to eradicate microorganisms. The MICs of CS and the CS NPs were determined using a broth microdilution method. Bacterial suspensions were adjusted to a turbidity of McFarland 0.5±0.05 and cultured overnight with different concentrations of CS or CS NPs. A control group without antimicrobial treatment was prepared as a reference. Following overnight incubation, solution turbidity was determined by visual inspection. Culture wells with no observable turbidity were further sub-cultured for MBC evaluation. Solutions from the clear wells were deposited onto an agar plate and cultured overnight to determine the MBCs.

As shown in Table 1 below, the MICs and MBCs of the CS NPs were generally equivalent to those of CS. Against some of the bacterial strains, the CS NPs unexpectedly showed a 2- to 4-fold enhancement in antimicrobial activity. It should be noted that PGA and PEG did not show any bacteriostatic or bactericidal effect, indicating that they did not contribute to the CS NPs' activity.

The results indicate that the therapeutic effect of CS was retained and, in some cases, unexpectedly improved upon nanoparticle assembly, offering a viable option against clinical manifestations of carbapenem-resistant bacteria.

TABLE 1

MICs and MBCs of CS and CS NPs against different bacteria

| | | | MIC (μg/mL) | | MBC (μg/mL) | |
|---|---|---|---|---|---|---|
| | Bacteria | | CS | CS NPs | CS | CS NPs |
| Reference Strains | *A. baumannii* 19606 | | 1 | 0.5 | 1 | 0.5 |
| | *A. baumannii* 17978 | | 1 | 0.5 | 1 | 0.5 |
| | *A. baumannii* 15151 | | 1 | 0.5 | 1 | 0.5 |
| | *P. aeruginosa* 27853 | | 1 | 1 | 1 | 1 |
| | *E. coli* 25922 | | 1 | 0.5 | 2 | 0.5 |
| Clinical carbapenem-resistant strains | *A. baumannii* | NHRI 1 | 1 | 0.5 | 2 | 1 |
| | | NHRI 2 | 1 | 1 | 2 | 1 |
| | | NHRI 3 | 1 | 1 | 1 | 4 |
| | | NHRI 4 | 1 | 1 | 2 | 2 |
| | | NHRI 5 | 1 | 1 | 1 | 1 |
| | *P. aeruginosa* | NHRI 1 | 2 | 2 | 2 | 4 |
| | | NHRI 2 | 2 | 2 | 4 | 4 |
| | | NHRI 3 | 2 | 2 | 8 | 2 |
| | | NHRI 4 | 4 | 2 | 8 | 4 |
| | | NHRI 5 | 2 | 2 | 4 | 4 |
| | *E. coli* | NHRI 1 | 1 | 1 | 1 | 1 |
| | | NHRI 2 | 1 | 0.5 | 1 | 0.5 |
| | | NHRI 3 | 1 | 0.5 | 1 | 0.5 |
| | | NHRI 4 | 1 | 0.5 | 2 | 0.5 |
| | | NHRI 5 | 1 | 0.5 | 2 | 0.5 |
| | | TSGH 2 | 1 | 0.5 | 1 | 0.5 |
| | | TSGH 4 | 1 | 0.5 | 1 | 0.5 |
| | | TSGH 6 | 1 | 0.5 | 2 | 0.5 |
| | | TSGH 8 | 1 | 0.5 | 2 | 0.5 |
| | | TSGH 10 | 1 | 0.5 | 1 | 0.5 |
| | | TSGH 14 | 1 | 0.5 | 1 | 0.5 |
| | | TSGH 20 | 1 | 1 | 1 | 1 |
| | | TSGH 21 | 1 | 0.5 | 1 | 0.5 |
| | *K. pneumoniae* | NHRI 1 | 2 | 2 | 4 | 2 |
| | | NHRI 2 | 2 | 2 | 2 | 8 |
| | | NHRI 4 | 2 | 2 | 2 | 2 |
| | | NHRI 5 | 2 | 2 | 2 | 2 |
| | | TSGH 1 | 2 | 1 | 2 | 1 |
| | | TSGH 3 | 1 | 1 | 1 | 2 |
| | | TSGH 5 | 1 | 1 | 1 | 1 |
| | | TSGH 7 | 1 | 1 | 1 | 1 |
| | | TSGH 9 | 1 | 0.5 | 2 | 1 |
| | | TSGH 11 | 4 | 4 | 4 | 2 |
| | | TSGH 13 | 1 | 1 | 2 | 1 |
| | | TSGH 15 | 1 | 1 | 1 | 1 |
| | | TSGH 16 | 2 | 0.5 | 2 | 1 |

TABLE 1-continued

MICs and MBCs of CS and CS NPs against different bacteria

| Bacteria | | MIC (μg/mL) | | MBC (μg/mL) | |
|---|---|---|---|---|---|
| | | CS | CS NPs | CS | CS NPs |
| | TSGH 17 | 1 | 1 | 1 | 1 |
| | TSGH 18 | 1 | 1 | 1 | 1 |
| | TSGH 19 | 1 | 1 | 4 | 1 |

Binding of CS NPs to Bacteria

A study was conducted to further examine the interaction between microorganisms and the CS NPs.

Figure 2:
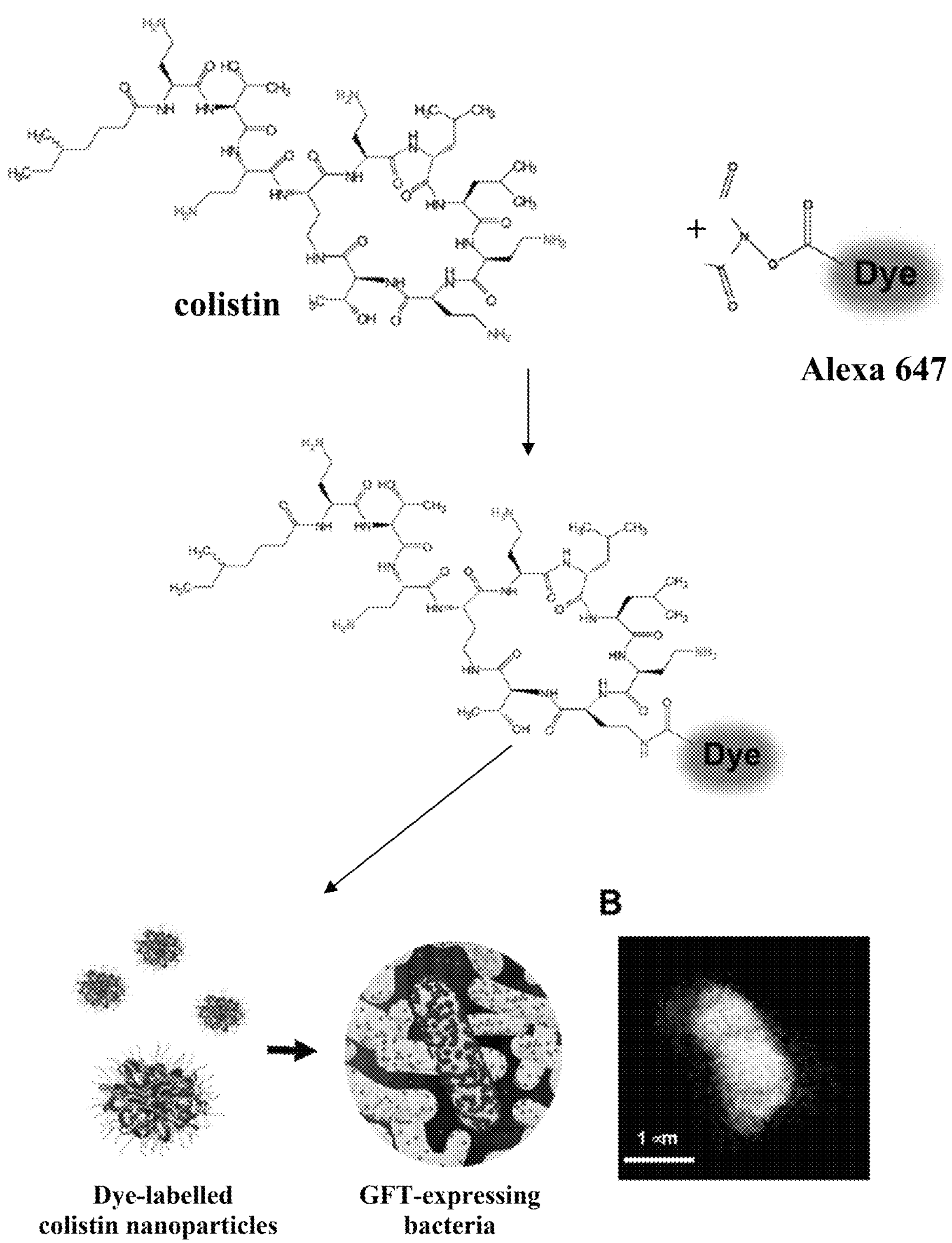
FIG. 2A is a schematic depiction of the preparation of CS NPs and their binding to green fluorescent protein (GFP)-expressing gram-negative bacteria.
FIG. 2B is a fluorescence microscopy image of *A. baumannii* with co-cultured with Alexa 647-conjugated CS NPs.
FIG. 2C shows fluorescence microscopy images of *A. baumannii* co-cultured with cyanine (Cy5)-conjugated CS NPs, in which the GFP visualized under the green channel to and the nanoparticles were visualized under the red channel.
FIG. 2D shows fluorescence microscopy images of *E. coli* co-cultured with Cy5-conjugated CS NPs, in which the GFP visualized under the green channel to and the nanoparticles were visualized under the red channel.
FIG. 2E is a graph that shows the normalized GFP and nanoparticle fluorescence signals within GFP-expressing *A. baumannii* measured following 1.5 hours of treatment with fluorescent CS NPs.
FIG. 2F is a graph that shows the normalized GFP and nanoparticle fluorescence signals within GFP-expressing *A. baumannii* measured following 24 hours of treatment with fluorescent CS NPs.
Figure 2:
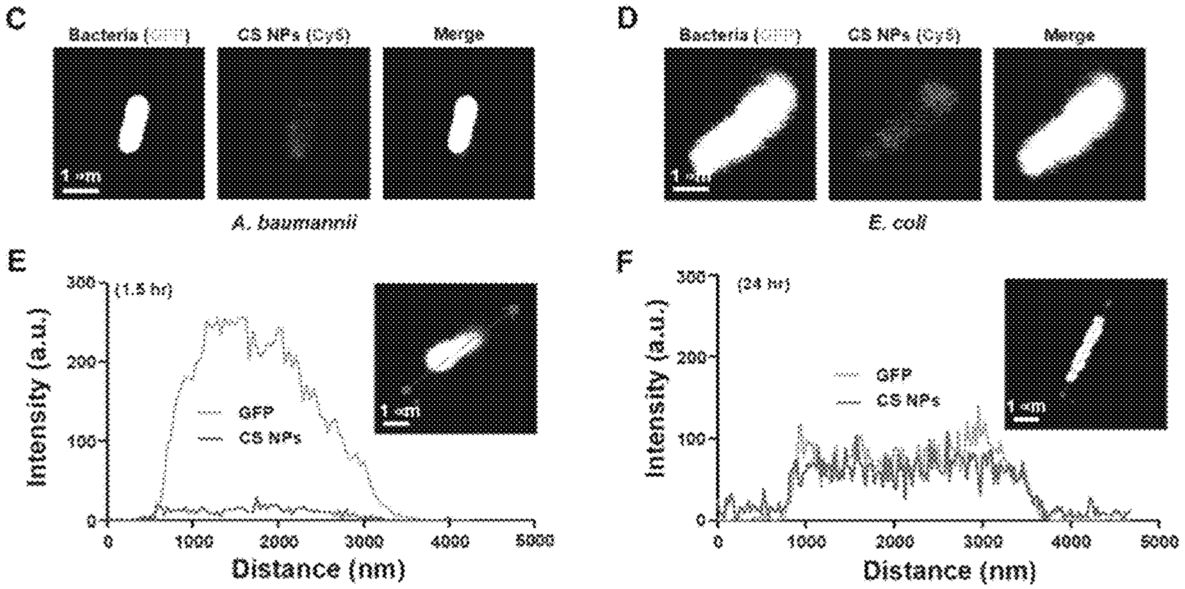

Briefly, fluorescent CS NPs were prepared by first incubating CS with Alexa Fluor 647 N-hydroxysuccinimidyl (NHS) ester at a 5 to 1 molar ratio in water for 48 hours. Following conjugation, CS was mixed with PGA and DSPE-PEG for nanoparticle assembly via dispersion by Nanolyzer N-2 at 5,000 psi. The resulting nanoparticles were filtered to remove non-conjugated fluorophore using a 30 kDa MWCO Amicon Ultra filter. Bluish retentate was collected, and the dye-labelled CS NPs were lyophilized and stored at −80° C. The fluorescent dye-labelled CS NPs were then suspended in PBS and incubated with GFP-expressing *A. baumannii* or *E. coli* (FIG. 2A). Following 90 minutes or 24 hours of incubation, the bacteria were washed with PBS to remove unbound nanoparticles. The resulting bacteria were fixed on poly-L-lysine coated slides with 4% paraformaldehyde and examined using a confocal fluorescence microscope (Zeiss LSM 700).

Following 90 minutes of treatment at the MIC of the CS NPs, confocal microscopy revealed bacterium cladded with fluorescent punctates (FIG. 2B). Nanoparticle attachment was observed with both *A. baumannii* (FIG. 2C) and *E. coli* (FIG. 2D), demonstrating affinity between gram-negative bacteria and the nanoparticles. In a kinetic study that subjected *A. baumannii* to 90 minutes and 24 hours of incubation with the CS NPs, prolonged incubation resulted in higher particle fluorescence across the bacterium (FIGS. 2E and 2F). This increase in particle fluorescence was accompanied by a reduction in GFP fluorescence. The equilibration of exterior particle and interior protein content suggests that the integrity of the bacterial cell wall was compromised. These observations support that the nanoparticles preserve the activity of CS. Following initial particle binding to the bacteria, the bacterial membranes were subsequently damaged, leading to growth inhibition.

Safety Profiles of CS NPs

A study was conducted to compare the safety profiles of the CS NPs and CS in mice.

Briefly, 8-week-old BALB/c mice, obtained from BioLASCO Taiwan Co., Ltd (Taipei, Taiwan), were injected with CS or the CS NPs intravenously through the tail vein with 8, 9, 10, 11, 12, 12.5, and 13 mg/kg of CS to determine the maximum tolerated dose (MTD) of the free drug and the nanoparticles. See e,g., Li et al, International Journal of Pharmaceutics, 2016, 515, 20-29; and Barnett et al., British Journal of Pharmacology and Chemotherapy, 1964, 23, 552-574. The highest dosage at which all examined subjects remained alive was defined as the MTD.

It was found that the MTD of the CS NPs and CS were 12.5 mg/kg and 10 mg/kg, respectively. At 12.5 mg/kg, CS induced tremors, breathing difficulty, and death within minutes in mice whereas the CS NPs were well tolerated by the animals (FIG. 3A).

To further compare the long-term treatment effects between CS and the CS NPs groups of three mice were subjected to comprehensive serum chemistry after 7 days of treatment (4 mg/kg, intravenous administration, twice a day) with the respective formulation (dissolved in PBS). A group of mice were injected intravenously with sterile PBS through the tail vein as negative control. 24 hours after the last treatment, 0.5 mL of blood was collected from the animals for comprehensive metabolic panel analysis. The data was analyzed by Student's t-test followed by Dunnett's multiple comparison tests using GraphPad Prism (GraphPad Software, San Diego, CA). p values smaller than 0.05 were considered significant.

Figure 3:
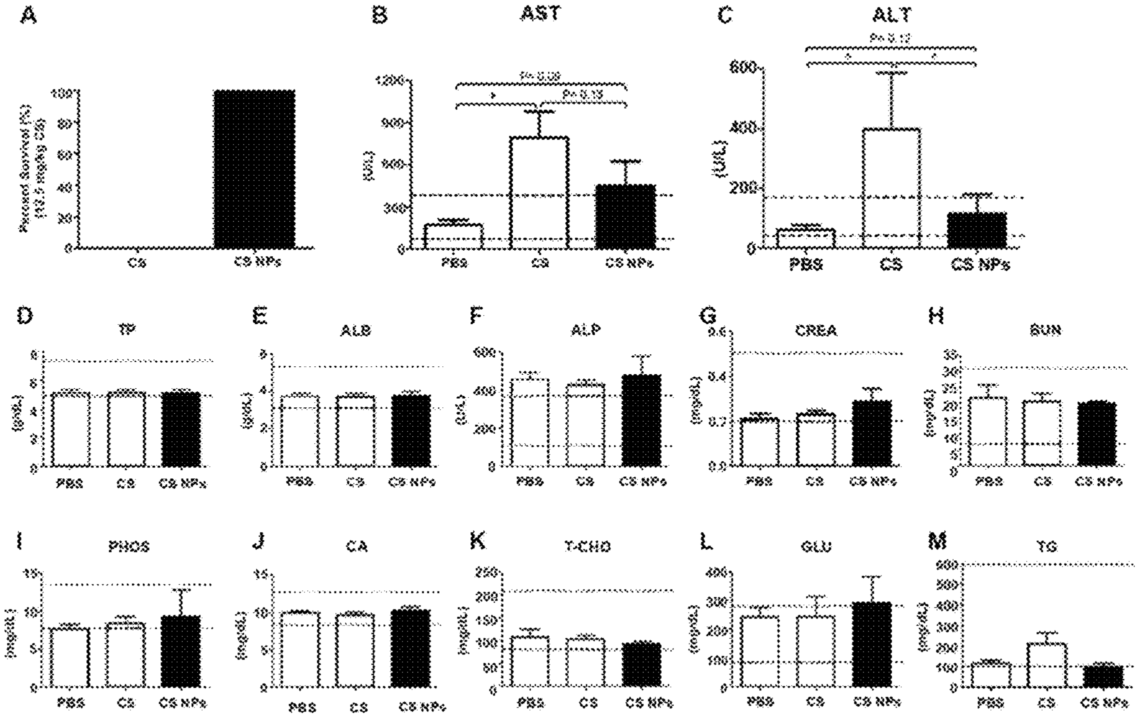
FIG. 3A is graph showing survival of mice following intravenous injections with 12.5 mg/kg of CS or CS NPs (n=6)
FIGS. 3B-3M are graphs respectively showing serum levels of aspartate transaminase (AST) alanine transaminase (ALT), total protein (TP), albumin (ALB), alkaline phosphatase (ALP), creatinine (CREA), blood urea nitrogen (BUN), phosphorus (PHOS), calcium (CA), total cholesterol (T-CHO), glucose (GLU), and triglyceride (TG) after treatment with PBS, CS, or CS NPs (dashed lines representing normal values and error bars representing means±s.e.m; n=3).

As shown in FIGS. 3B and 3C, CS treatment significantly increased the aspartate aminotransferase (AST) and alanine aminotransferase (ALT) levels, which are indicators of liver damage, as compared to the PBS control. This finding is consistent with prior reports that showed clinical cases of hepatotoxicity associated with CS and CS derivatives. See Kalin et al., *Infection,* 2014, 42, 37-42; Katz et al., *Med. Ann. D. C.,* 1963, 32, 408-413; and Falagas et al., *Crit. Care,* 2006, 10, R27. By contrast, the CS NPs resulted in reduced ALT and AST values as compared to CS. Among the other parameters in the comprehensive metabolic panel (FIGS. 3D-3M), neither CS nor the CS NPs induced any notable changes. These results indicate that the CS NPs are safer to administer, and the additional PGA and DSPE-PEG do not elicit any unanticipated adverse effect. It is worth noting that no sign of nephrotoxicity, a reported side effect of CS, was observed in this study, with the levels of creatinine (CREA) and blood urea nitrogen (BUN) being similar among the PBS, CS, and CS NP treatment groups.

In sum, the results indicate that nanoparticle assembly unexpectedly improved CS's MTD and reduced liver toxicity.

In Vivo Antimicrobial Activity of CS NPs

The in vivo antimicrobial activity of the CS NPs was further assessed in a murine model of *A. baumannii* pneumonia. See Yang et al., *Antimicrobial Agents and Chemotherapy,* 2016, 60, 4047-4054.

Briefly, *A. baumannii* 17978 were grown in 30 mL LB broth under shaking at 37° C. to reach the mid-logarithmic phase. The bacteria were then pelleted by centrifugation at 4,000 g for 15 minutes. The bacteria pellet was resuspended in PBS and mixed with 5% mucin derived from porcine stomach (type 3; Sigma-Aldrich, Taiwan).

Figure 4:
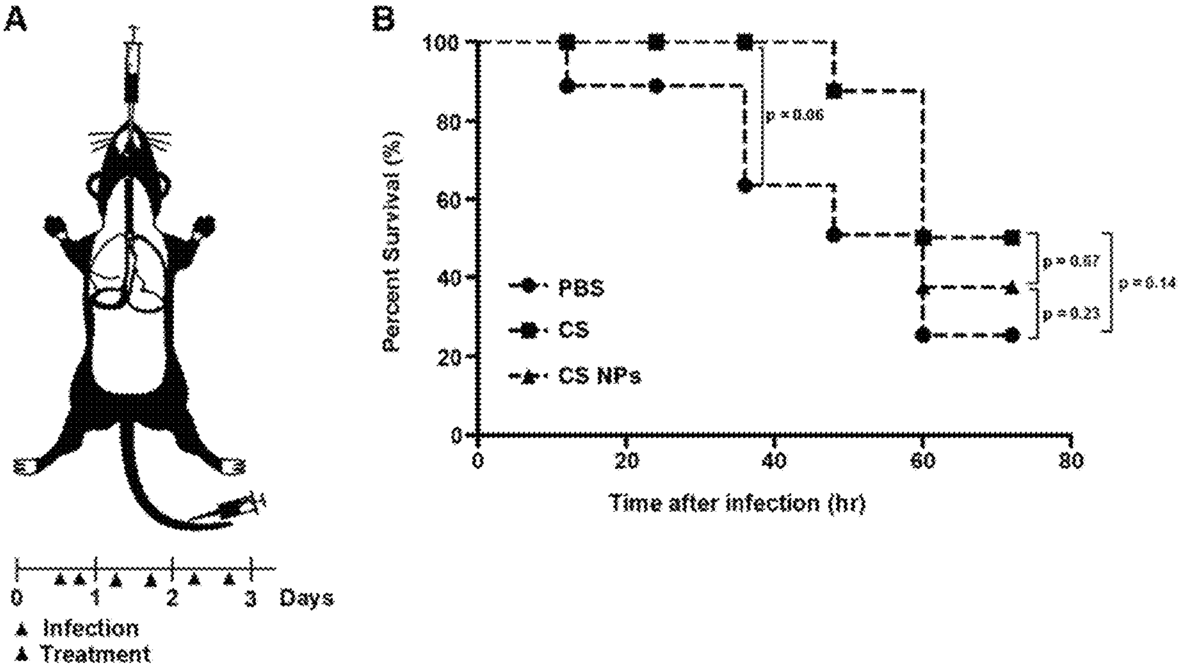
FIG. 4A is a schematic depiction of CS NP treatment in a mouse model of *A. baumannii* pneumonia and its treatment schedule
FIG. 4B is a graph showing post-infection survival for three different treatment groups, i.e., mice treated with 5 mg/kg of CS, 5 mg/kg of CS NPs, or phosphate-buffered saline (PBS) as a control.

To induce *A. baumannii* pneumonia, 8-week-old C57BL/6 mice (National Laboratory Animal Center, Taiwan) were first anesthetized with 2% tribromoethanol (Avertin; 0.018 mL/g). $6.07 \times 10^8$ CFU of *A. baumannii* 17978 were then administered to the mice via intra-tracheal injection to induce pneumonia (FIG. 4A). At 2 hours post-inoculation, the mice were treated twice a day with PBS (as the control), CS, or CS NPs at 5 mg/kg via intravenous injections.

The efficacy between CS and the CS NPs was compared by survival analysis. The difference in survival among the groups was analyzed by a Log-rank test using GraphPad Prism. Treatment efficacy of CS and CS NPs was observed 36 hour post-infection as no mortality was recorded in either of the two drug treatment groups whereas 37.5% of the control group animals were deceased. Following 72 hours of observation, the CS NPs showed treatment efficacy similar to that of CS (p=0.67) with 3 versus 4 surviving mice out of 8 assessed animals in each of the two treatment groups (FIG. 4B). The survival outcome supports retention of CS's antimicrobial activity following nanoparticle assembly.

These results indicate that the CS NPs of this invention unexpectedly exhibited therapeutic efficacy in treating drug-resistant bacteria with a desirable safety profile.

Example 2: Nanoparticles Formed from CS, PGA, and DSPE-PEG5000

A study was performed as follows for preparing, characterizing, and testing therapeutic nanoparticles formed from CS, PGA, and DSPE-PEG5000 (MW 5000).

Therapeutic nanoparticles were prepared according to the procedure described in EXAMPLE 1, which was modified as described below. More specifically, a CS to PGA ratio of 6:7 (w/w) was adopted and the nanoparticles were stabilized in 1.5% of DSPE-PEG5000. The additional amount of PGA and the PEG of a higher molecular weight were used to enhance stability of the CS NPs.

In a typical preparation, 6 mg of CS and 7 mg of PGA were mixed in 12 mL of water containing 180 mg of DSPE-PEG5000. The resulting mixture was then dispersed using a high-pressure homogenizer and the resulting nanoparticles were filtered. The nanoparticles thus collected were assessed for size and zeta potential by DLS and subsequently lyophilized for storage at −80° C. All other experiments were performed with lyophilized CS NPs resuspended in PBS. DLS analysis showed that the nanoparticles were 12.5 nm in diameter, −5 mV in zeta potential, and were stable following lyophilization and resuspension (Table 2).

In Table 2, "Z-Ave" refers the cumulants mean, and "PDI" refers to polydispersity index.

TABLE 2

Physicochemical properties of CS NPs as determined by DLS

| CS NPs | Before Lyophilization | | | | After Lyophilization | | | |
|---|---|---|---|---|---|---|---|---|
| | Z-Ave (d · nm) | Size (d · nm) | PDI | Zeta Potential (mV) | Z-Ave (d · nm) | Size (d · nm) | PDI | Zeta Potential (mV) |
| CS:PGA = 60:70 1.5% m-PEG (5000) | 22.54 ± 0.26 | 12.52 ± 0.48 | 0.36 ± 0.03 | −5.10 ± 0.68 | 19.82 ± 0.12 | 12.30 ± 0.39 | 0.23 ± 0.01 | −3.72 ± 0.60 |

HPLC quantification shows that the CS NPs have a high encapsulation efficiency (EE %) of colistin A and colistin B (Table 3).

TABLE 3

CS encapsulation efficiency by CS NPs as measured by HPLC

| CS NPs | Colistin A | Colistin B | PEG |
|---|---|---|---|
| EE % | 99.1 ± 4.4 | 98.9 ± 3.0 | 94.6 ± 3.6 |

Antibacterial Efficacy of Nanoparticles Formed from CS, PGA, and DSPE-PEG5000

To evaluate the antibacterial efficacy of the CS NPs of this study, their MIC and MBC were assessed against 5 reference bacterial strains and 20 clinical isolates of carbapenem-resistant *A. baumannii, E. coli, K. pneumoniae*, and *P. aeruginosa* according to the procedures set forth in EXAMPLE 1. Reference bacterial stains were purchased from ATCC. Carbapenem-resistant clinical isolated were obtained from NHRI.

As shown in Table 4, the additional amounts of polymers, as compared to those used in EXAMPLE 1, did not affect the antimicrobial activity of the resulting CS NPs. Indeed, they exhibited antimicrobial activity comparable to that of CS. It should be noted that PGA and DSPE-PEG did not show any bacteriostatic or bactericidal effect, indicating that they did not contribute to the CS NPs' activity.

TABLE 4

MICs and MBCs of CS and CS NPs against different bacteria

| | Bacteria | | MIC (μg/mL) | | MBC (μg/mL) | |
|---|---|---|---|---|---|---|
| | | | CS | CS NPs | CS | CS NPs |
| Reference Strains | *A. baumannii* 19606 | | 2 | 1 | 4 | 4 |
| | *A. baumannii* 17978 | | 2 | 2 | 2 | 4 |
| | *P. aeruginosa* 27853 | | 1 | 0.5 | 2 | 1 |
| | *E. coli* 25922 | | 1 | 0.5 | 2 | 1 |
| Clinical carbapenem-resistant isolates | *A. baumannii* | NHRI 1 | 1 | 1 | 2 | 8 |
| | | NHRI 2 | 2 | 4 | 2 | 4 |
| | | NHRI 3 | 1 | 1 | 2 | 4 |
| | | NHRI 4 | 1 | 1 | 4 | 8 |
| | | NHRI 5 | 1 | 1 | 2 | 2 |
| | E. *coli* | NHRI 1 | 2 | 0.5 | 2 | 1 |
| | | NHRI 2 | 1 | 0.5 | 2 | 1 |
| | | NHRI 3 | 1 | 0.25 | 2 | 0.5 |
| | | NHRI 4 | 1 | 1 | 1 | 1 |
| | | NHRI 5 | 0.5 | 0.5 | 0.5 | 0.5 |
| | *K. pneumoniae* | NHRI 1 | 1 | 0.5 | 4 | 1 |
| | | NHRI 2 | 1 | 1 | 1 | 2 |
| | | NHRI 3 | 1 | 0.5 | 2 | 4 |
| | | NHRI 4 | 2 | 0.5 | 2 | 2 |
| | | NHRI 5 | 1 | 0.5 | 4 | 4 |
| | *P. aeruginosa* | NHRI 1 | 1 | 0.5 | 4 | 4 |
| | | NHRI 2 | 2 | 1 | 4 | 8 |
| | | NHRI 3 | 1 | 0.5 | 4 | 4 |
| | | NHRI 4 | 2 | 1 | 4 | 8 |
| | | NHRI 5 | 1 | 0.5 | 4 | 4 |

Examination of CS NP Binding to Bacteria

Figure 5:
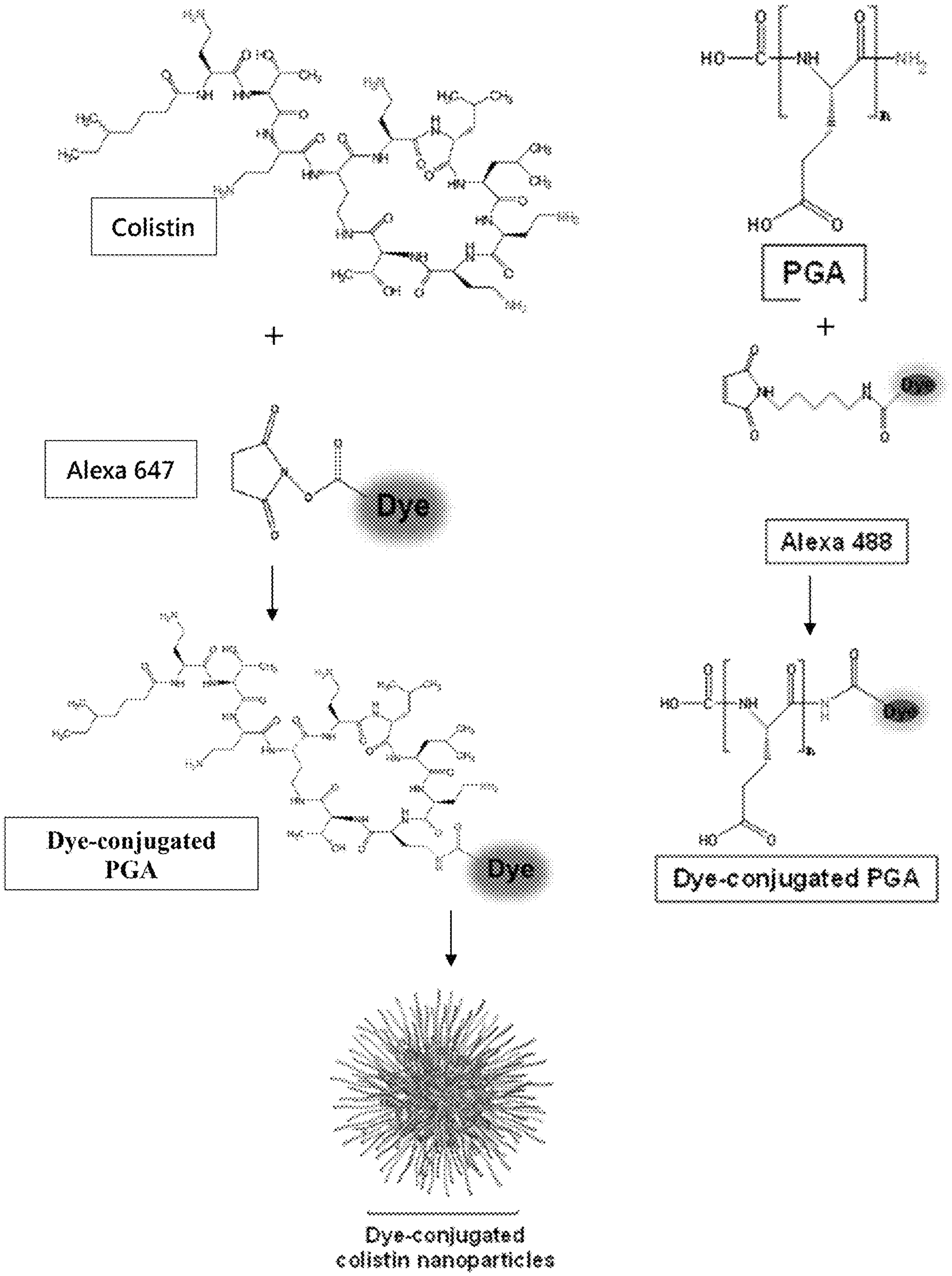
FIG. 5A is a schematic depiction of the preparation and quantitative analysis of the Alexa 647 and Alexa 488 fluorophore-conjugated CS NPs, described in EXAMPLE 2.
FIG. 5B is a graph showing the relative fluorescence intensity of Alexa 647 and Alexa 488 in bacterial pellets following 1.5 and 24 hours of bacterial incubation with the fluorophore-conjugated CS NPs (error bars represent means±standard deviation; n=3).
Figure 5:
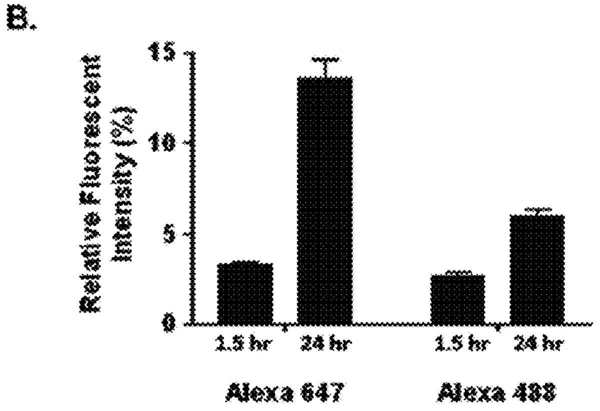

A study was conducted to examine the interaction between bacteria and the CS NPs, which contain additional amounts of polymers as compared to the CS NPs described in EXAMPLE 1(FIG. 5A).

Fluorophore-conjugated-CS was prepared by incubating CS with Alexa Fluor 647 NHS at a 5 to 1 molar ratio in 0.1 M sodium bicarbonate buffer for 72 hours. Fluorophore-conjugated PGA, on the other hand, was prepared by incubating PGA with and Alexa Fluor 488 NHS ester at 1 to 7.5 molar ratio in 0.1 M sodium bicarbonate buffer for 72 hours.

Following the fluorophore-conjugation, CS and PGA were mixed in water containing DSPE-PEG. The mixture was then dispersed using a Nanolyzer N-2 at 5,000 psi. The resulting fluorophore-conjugated nanoparticles were filtered to remove non-conjugated fluorophore using a 30 kDa MWCO Amicon Ultra filter. Fluorescent retentate was collected, and the fluorophore-conjugated nanoparticles were lyophilized and stored at −80° C.

An overnight culture of *E. coli* ATCC 25922 was pelleted at 10,000×g for 10 min at 4° C. and resuspended in PBS. Bacterial suspensions were mixed with fluorophore-conjugated CS or fluorophore-conjugated CS NPs and incubated at 37° C. As negative controls, bacterial suspensions in the absence of CS or CS NP incubation were prepared. After 1.5 and 24 hours of co-incubation with fluorophore-conjugated CS or fluorophore-conjugated CS NPs, the bacteria were washed with PBS. The samples were lyophilized and resuspended with 1% sodium dodecyl sulfate (Sigma-Aldrich) (w/v) and measured for the CS content with a microplate fluorescence reader (TECAN Infinite M1000, Austria).

The fluorescence of both Alexa 647 and 488 increased in intensity after 24 hours of co-incubation, indicating that CS in the CS NPs readily interacted with bacteria (FIG. 5B). In other words, the additional amount of polymers did not interfere with the CS NPs' bacteria-binding function.

Determination of the MTD of CS NPs

A dose-escalation study in mice was conducted to determine the MTD of the CS NPs.

For this study, mice (8 weeks, Balb/c mice) were obtained from Bio-LASCO Taiwan Co., Ltd (Taipei, Taiwan). To assess the MTD of the nanoparticles, the mice were injected with CS or CS NPs intravenously through the tail vein with 25, 40, 45, and 50 mg/kg of CS base (n=10). The highest dosage at which all examined subjects remained alive was defined as the MTD.

Figure 6:
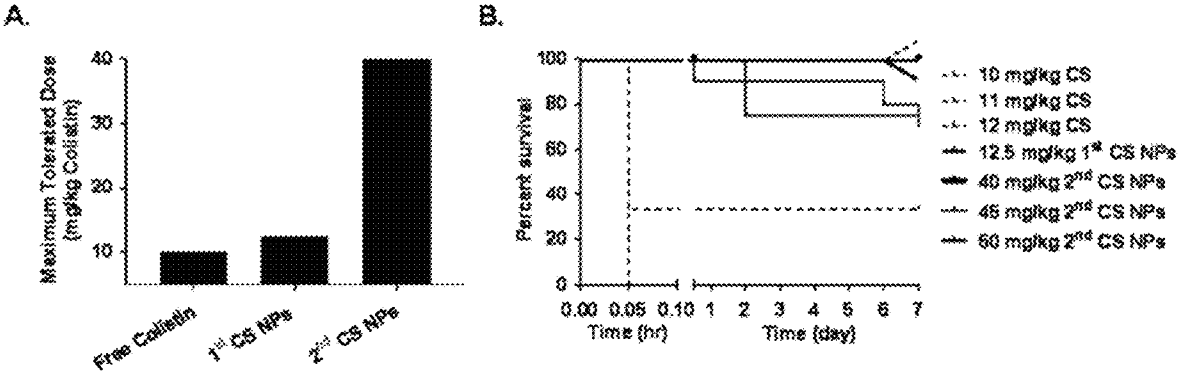
FIG. 6A is a bar graph showing the MTD for CS, the CS NPs of EXAMPLE 1 ($1^{st}$ CS NPs), and those of EXAMPLE 2 ($2^{nd}$ CS NPs) measured at 10 mg/kg, 12.5 mg/kg, and 40 mg/kg, respectively.
FIG. 6B is a graph showing the survival of mice following intravenous injections with CS (10 mg/kg, 11 mg/kg, and 12 mg/kg), the $1^{st}$ CS NPs (12.5 mg/kg), and the $2^{nd}$ CS NPs (40 mg/kg, 45 mg/kg, and 50 mg/kg).

As shown in FIG. 6, the CS NPs of this study exhibited an MTD of 40 mg/kg, more than 3-folds higher than that of CS and more than 2-folds higher than that of the CS NPs of EXAMPLE 1 (FIG. 6). The increased MTD allows for higher drug administration for treating drug-resistant isolates in clinics.

CS NP Treatment in a Mouse Survival Model of *K. pneumoniae* Infection

Figure 7:
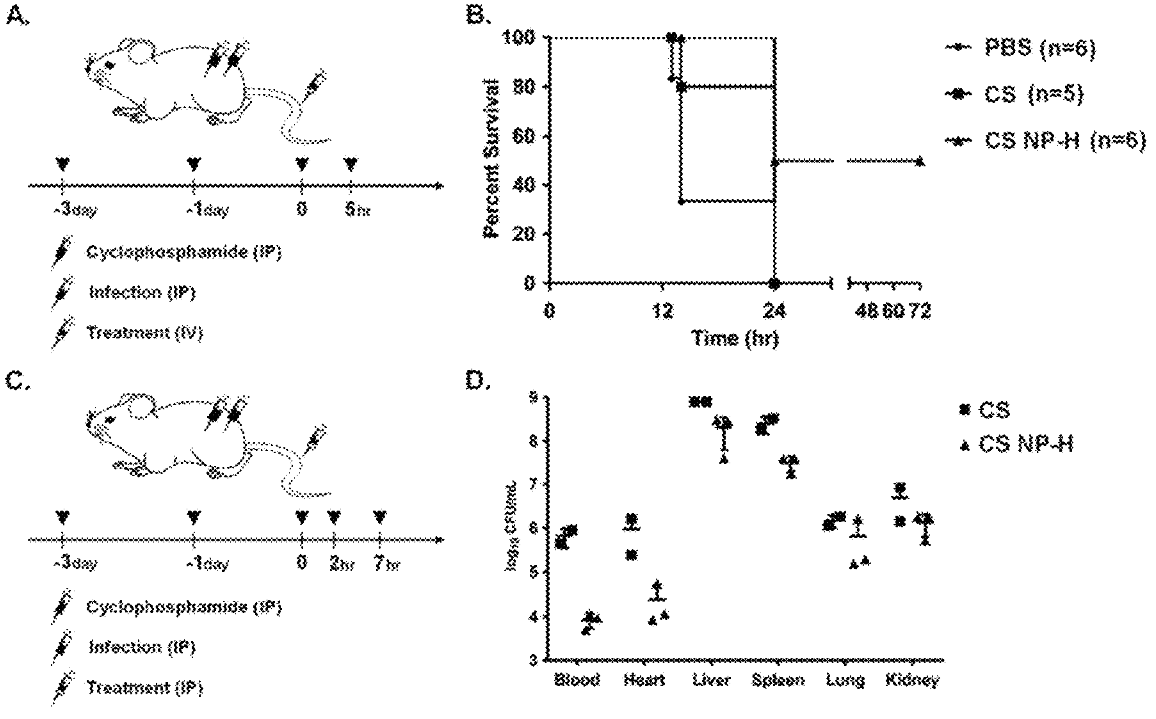
FIG. 7A is a schematic depiction of CS NP treatment in a mouse survival model of *K. pneumoniae* NHRI 1 isolate and its treatment schedule.
FIG. 7B is a graph showing the survival for three treatment groups, i.e., mice treated with PBS, 5 mg/kg of CS, 20 mg/kg CS NPs, which was monitored and analyzed using a Log-rank test (n=5-6)
FIG. 7C is a schematic depiction of CS NP treatment in a mouse infectious model of *K. pneumoniae* NHRI 1 isolate and its treatment schedule.

A mouse infectious model with *K. pneumoniae* was adopted to validate the antimicrobial activity of CS NPs in vivo (FIG. 7A).

Mice (20-22 g, 10 weeks, Balb/c mice) were obtained from Bio-LASCO Taiwan Co., Ltd (Taipei, Taiwan). 3 days and 1 day before infection, the mice were injected intraperitoneally with 150 and 100 mg/kg of cyclophosphamide, respectively, to induce neutropenia. *K. pneumoniae* NHRI 1 isolate was grown in 60 mL Mueller Hinton broth at 150 rpm (orbital shaker, Yihder TS-580) for 2.5 hours at 37° C. to reach the mid-logarithmic phase. The bacteria were then collected at 10,000×g for 10 minutes at 4° C. The bacterial pellet was resuspended in PBS. To induce *K. pneumoniae* intraperitoneal infection with a lethal bacterial dose, mice were infected with $1.5\times10^8$ CFU/mouse in 50 mL via intraperitoneal injection. 5 hours post-infection, the infected mice were treated with 5 mg/kg CS (50% MTD), 20 mg/kg CS NPs (50% MTD), or PBS as a control.

It was found that the high-dose treatment enabled by the CS NPs improved mice survival rate from 0% to 50%, whereas CS did not improve survival of infected mice (FIG. 7B).

CS NP Treatment in a Mouse Infectious Model with *K. pneumoniae*

To compare the efficacy between CS and CS NPs, a bacterial enumeration study was further performed in a non-lethal bacterial challenge (FIG. 7C).

Mice (20-22 g, 10 weeks, Balb/c mice, 3 in each group) were obtained from Bio-LASCO Taiwan Co., Ltd (Taipei, Taiwan). 3 days and 1 day before infection, the mice were injected intraperitoneally with 150 and 100 mg/kg of cyclophosphamide, respectively, to induce neutropenia. *K. pneumoniae* NHRI 1 isolate was grown in 60 mL Mueller Hinton broth at 150 rpm (orbital shaker, Yihder TS-580) for 2.5 hours at 37° C. to reach the mid-logarithmic phase. The bacteria were then collected at 10,000×g for 10 minutes at 4° C. The bacterial pellet was resuspended in PBS. To induce *K. pneumoniae* intraperitoneal infection, mice were infected with $8.4\times10^7$ CFU/mouse in 50 mL via intraperitoneal injection. 2 hours and 7 hours post-infection, the infected mice were treated with 5 mg/kg CS or 20 mg/kg CS NPs intravenously. 24 hours post-infection, the mice were sacrificed and their tissues were collected for bacterial enumeration. Efficacy of the two treatments was compared by the number of CFUs in tissue examined.

By examining the bacteria count from different organs derived from mice receiving two treatments of CS or CS NPs at their corresponding 50% MTD, a 2-log reduction in bacteria count in the blood and heart of the CS NP-treated group was observed (FIG. 7D).

The results indicate that, compared to CS, the CS NPs of this invention unexpectedly demonstrated much safer profiles without affecting antimicrobial activity.

Example 3: Nanoparticles Formed from CS, an Oligonucleotide, and DSPE-PEG5000

A study was performed for preparing, characterizing, and testing therapeutic nanoparticles formed from CS, an oligonucleotide, and DSPE-PEG5000.

A fluorescent 20-mer double-stranded DNA was used as the oligonucleotide. To prepare the fluorescent 20-mer double-stranded DNA, oligo strand with fluorescein amidite (FAM) (5'-/56-FAM/TT GGC TAC GTC CAG GAG CGC-3') was mixed with another forward oligo strand without fluorescent dye and annealed with reverse oligo strand at 94° C. and cooled gradually. To prepare the nanoparticles containing CS and the oligonucleotide (CS/DNA NPs), CS was mixed with the oligonucleotide at a 6:7 (w:w) ratio and stabilized in 1.5% of DSPE-PEG5000.

In a typical preparation, 6 mg of CS and 7 mg of the oligonucleotide were mixed in 12 mL of water containing 1.5% of DSPE-PEG5000. The mixture was then dispersed using a Nanolyzer N-2 at 5,000 psi. The resulting nanoparticles were filtered to remove free CS, oligonucleotide and DSPE-PEG5000 using a 30 kDa MWCO Amicon Ultra filter. Successful preparation of CS/DNA NPs was verified upon observation of fluorescent retentate, which indicated that the fluorescently labelled DNA was not removed by the size-exclusion filter. Fluorescent yellow retentate was collected, and the CS/DNA nanoparticles were lyophilized and stored at −80° C. DLS measurements revealed that the nanoparticles were 10.75 nm in size, had a slightly negative zeta potential, and stable upon lyophilization. See Table 5 below.

For the definitions of "Z-Ave", and "PDI", see EXAMPLE 2 above.

TABLE 5

| Physicochemical properties of CS/DNA nanoparticles as measured by DLS | | | | | | | | |
|---|---|---|---|---|---|---|---|---|
| | Before Lyophilization | | | | After Lyophilization | | | |
| CS/DNA NPs | Z-Ave (d · nm) | Size (d · nm) | PDI | Zeta Potential (mV) | Z-Ave (d · nm) | Size (d · nm) | PDI | Zeta Potential (mV) |
| CS:DNA = 60:70 1.5% m-PEG (5000) | 24.66 ± 0.52 | 10.75 ± 0.39 | 0.58 ± 0.03 | −4.21 ± 0.13 | 24.23 ± 0.12 | 13.55 ± 0.38 | 0.38 ± 0.03 | −7.85 ± 1.39 |

Figure 8:
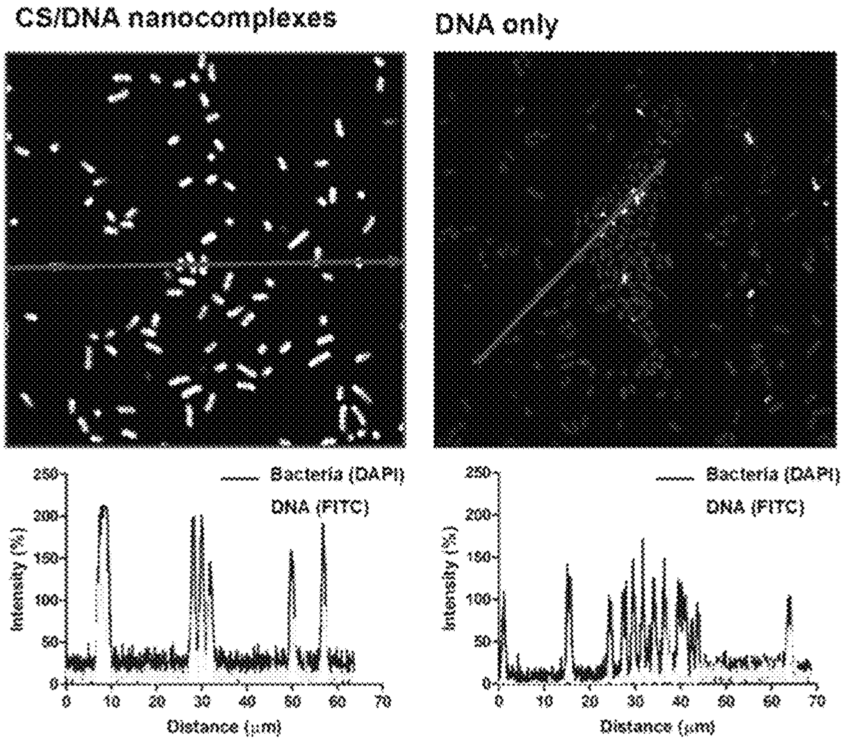
FIG. 8 shows fluorescence microscopy images of carbapenem-resistant *K. pneumoniae*, stained with 4'-6-diamidino-2-phenylindole following incubation with CS/DNA nanoparticles (left) and DNA only (right).

To observe the interaction between microorganisms and the CS/DNA NPs, the nanoparticles were suspended in PBS and incubated with carbapenem-resistant *Klebsiella pneumoniae*. As a control, free DNA was also incubated with the bacteria. Following 3 hours of incubation, the bacteria were washed with PBS to remove unbound nanoparticles. The resulting bacteria were fixed on poly-L-lysine coated slides with 4% paraformaldehyde and examined using a confocal fluorescence microscope (Zeiss LSM 700). The study revealed that the CS/DNA NPs delivered a large amount of DNA into the bacteria. By contrast, little DNA was associated with the bacteria in the control group (FIG. 8).

To demonstrate that therapeutically relevant oligonucleotides, such as antisense oligonucleotides (ASOs), can be incorporated into CS NPs for enhanced antimicrobial treatment, a study was conducted to prepare and test CS NPs containing ASOs of ftsZ DNA fragment ($ASO_{ftsZ}$), the blocking of which reduces the cell division of prokaryotes. Successful delivery of ftsZ-targeted ASOs can block prokaryotic ftsZ gene and inhibit bacteria colony formation.

For this study, cyanine-labelled $ASO_{ftsZ}$ (Cy5-$ASO_{ftsZ}$) was synthesized and used to form coacervation complexes with Alexa 488-conjugated CS (Alexa488-CS) for nanoparticle preparations. The recovery yields of Alexa488-CS and Cy5-$ASO_{ftsZ}$, as measured using a plate reader (TECAN infinite M1000 PRO) were 89.5% and 71.13%, respectively.

Figure 9:
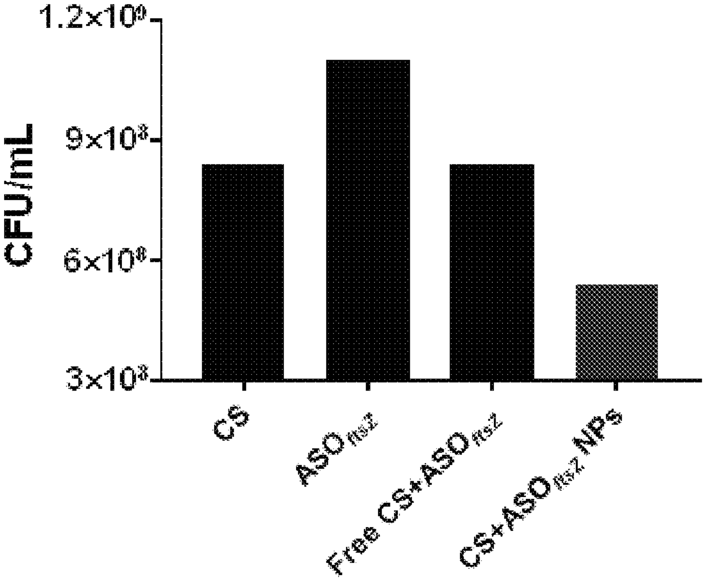
FIG. 9 is a bar graph showing *E. coli* ATCC25922 colony formation after 24 hours of co-culture with CS, antisense oligonucleotide of ftsZ DNA fragment ($ASO_{ftsZ}$), CS+$ASO_{ftsZ}$, and CS-$ASO_{ftsZ}$ nanoparticles (CS-$ASO_{fstZ}$ NPs).

MIC and MBC of Alexa488-CS and double fluorophore-labelled CS NPs (CS-$ASO_{ftsZ}$ NPs) were assessed against *E. coli* ATCC 25922, and the results show that the incorporation of $ASO_{ftsZ}$ did not affect the MIC and MBC of CS (Table 6). In addition, at 1 μg/mL, which was less than the MIC of CS, the CS-$ASO_{ftsZ}$ NPs exhibited synergistic antibacterial effect (FIG. 9).

TABLE 6

MIC and MBC of different treatments against *E. Coli* ATCC 25922.

| Treatments | MIC (μg/mL) | MBC (μg/mL) |
|---|---|---|
| CS | 2 | 4 |
| $ASO_{ftsZ}$ | >2 | >2 |
| CS + $ASO_{ftsZ}$ | 2 | 2 |
| CS – $ASO_{ftsZ}$NP | 2 | 2 |

To observe the interaction between microorganisms and CS-$ASO_{ftsZ}$ NPs, these nanoparticles, suspended in PBS, were incubated with *E. coli*. ATCC 25922. Following 2 hours of incubation, the bacteria were washed with PBS to remove unbound nanoparticles. The bacteria were then fixed on poly-L-lysine coated slides with 4% paraformaldehyde and examined using a confocal fluorescence microscope (Inverted Confocal plus Super Resolution Microscope; LSM 780+ELYRA).

Following bacterial incubation with CS-$ASO_{ftsZ}$ NPs or with a free CS/free $ASO_{ftsZ}$ mixture, significantly different CS and $ASO_{ftsZ}$ distributions were observed. More specifically, incubation with free CS and free $ASO_{ftsZ}$ resulted in CS and $ASO_{ftsZ}$ localization on the bacterial edge, whereas incubation with the nanoparticles resulted in CS and $ASO_{ftsZ}$ distribution in the entire bacterium. Successful $ASO_{ftsZ}$ delivery by the CS-$ASO_{ftsZ}$ NPs also resulted in high DNA content, as evidenced by increased 4',6-diamidino-2-phenylindole staining.

These results indicate that ASOs can be used as biopolymers for CS NP preparation, and CS NPs can facilitate delivery of ASOs into bacteria. They also indicate that synergistic effect can be achieved by coupling therapeutically relevant ASO with CS for nanoparticle formation, and in the case of $ASO_{ftsZ}$, successful delivery can influence bacterial division, thereby resulting in higher accumulation of bacterial DNA.

Example 4: Nanoparticles Formed from CS and methoxy-poly(ethylene glycol)-block-poly(L-aspartic Acid Sodium Salt) ($mPEG_{20K}$-b-$PLD_{75}$)

CS NPs were also prepared using CS and a diblock copolymer, i.e., $mPEG_{20K}$-b-$PLD_{75}$. The ratio of diblock copolymer to CS was 2:3 (w/w). Briefly, colistin and the diblock copolymer mixed at a ratio of 2:3 (w/w) to form coacervation complexes, which were further dispersed by Nanolyzer N-2 at 5,000 psi. The resulting nanoparticles were filtered to remove free colistin and free copolymer using a 30 kDa MWCO Amicon Ultra filter. The collected nanoparticles were lyophilized and stored at −80° C.

The resulting nanoparticles, i.e., CS/$mPEG_{20K}$-b-$PLD_{75}$ NPs, were around 60 nm in size as determined by DLS analysis. This formulation was stable and consistent in size and zeta potential after lyophilization. See Table 7 below.

Again, see EXAMPLE 2 above for the definitions of "Z-Ave", and "PDI".

TABLE 7

| Physicochemical properties of CS/mPEG$_{20K}$-b-PLD$_{75}$ NPs as determined by DLS | | | | | | | | |
|---|---|---|---|---|---|---|---|---|
| | Before Lyophilization | | | | After Lyophilization | | | |
| CS/mPEG$_{20K}$-b-PLD$_{75}$ NPs | Z-Ave (d · nm) | Size (d · nm) (% Number) | PDI | Zeta Potential (mV) | Z-Ave (d · nm) | Size (d · nm) (% Number) | PDI | Zeta Potential (mV) |
| CS:mPEG$_{20k}$-b-PLD$_{75}$ = 20:30 | 114.7 | 66.89 | 0.161 | −1.25 | 98.92 | 61.41 | 0.183 | 0.971 |

The encapsulation efficiency of CS was very high upon nanoparticle preparation with recovery yields of colistin A and colistin B at 97.6% and 64.2%, respectively, as measured by HPLC analysis. Upon cryoEM observation, it was found that the formulation yielded nanoparticles approximately 10 nm in size. There were several large nanoparticles that skewed the size determination by DLS (Table 7). The MTD of nanoparticles of this study was 17.5 mg/kg, indicating that they are safer than CS (MTD=10 mg/kg).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further, from the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A therapeutic nanoparticle, comprising:
a cationic polypeptide,
a polyanionic molecule, and
a polyethyleneglycol (PEG) lipid,
wherein the therapeutic nanoparticle has a hydrodynamic diameter of less than 50 nm,
wherein the cationic polypeptide is colistin,
wherein the polyanionic molecule is an anionic polypeptide or an anionic oligonucleotide of less than 500 base pairs;
wherein the PEG lipid is selected from the group consisting of DSPE-PEG, DSPE-PEG-Maleimide, DSPE-PEG-Biotin, mPEG-Cholesterol, and Cholesterol-PEG-Amine; and
wherein the colistin to polyanionic molecule is present at a charge ratio of 1:4 to 7:1 (cation:anion).

2. The therapeutic nanoparticle of claim 1, wherein the polyanionic molecule is a polyamino acid formed from glutamic acid or aspartic acid.

3. The therapeutic nanoparticle of claim 1, wherein the polyanionic molecule is a single- or double-stranded DNA, an RNA, or a locked nucleic acid.

4. The therapeutic nanoparticle of claim 3, wherein the polyanionic molecule is a 20-mer double-stranded DNA.

5. The therapeutic nanoparticle of claim 1, wherein the therapeutic nanoparticle has a diameter of less than 25 nm.

6. The therapeutic nanoparticle of claim 5, wherein the therapeutic nanoparticle has a diameter of less than 15 nm.

7. A pharmaceutical composition, comprising a therapeutic nanoparticle of claim 1 and a pharmaceutically acceptable carrier.

8. A method of preparing a therapeutic nanoparticle of claim 1, the method comprising:
providing an aqueous solution that contains a PEG lipid selected from the group consisting of DSPE-PEG, DSPE-PEG-Maleimide, DSPE-PEG-Biotin, mPEG-Cholesterol, and Cholesterol-PEG-Amine, mixing into the aqueous solution a cationic polypeptide and a polyanionic molecule at a charge ratio of 1:4 to 7:1, and obtaining a therapeutic nanoparticle from the resulted mixture;
wherein the cationic polypeptide is colistin,
wherein the polyanionic molecule is an anionic polypeptide or an anionic, oligonucleotide of less than 500 base pairs.

* * * * *